United States Patent [19]
Guthrie et al.

[11] Patent Number: 5,198,749
[45] Date of Patent: Mar. 30, 1993

[54] SINGLE-USE DISPOSABLE MOLTEN METAL INCLUSION SENSOR

[75] Inventors: Roderick I. L. Guthrie, Montreal, Canada; Hidemasa Nakajima, Kashima, Japan

[73] Assignees: R. Guthrie Research Associates Inc., Quebec, Canada; Sumitomo Metal Industries Ltd., Osaka, Japan

[21] Appl. No.: 768,714
[22] PCT Filed: Apr. 27, 1990
[86] PCT No.: PCT/CA90/00140
§ 371 Date: Oct. 28, 1991
§ 102(e) Date: Oct. 28, 1991
[87] PCT Pub. No.: WO90/13014
PCT Pub. Date: Nov. 1, 1990

[30] Foreign Application Priority Data
Apr. 27, 1989 [JP] Japan .................................. 1-108871

[51] Int. Cl.$^5$ ............................................ G01N 27/02
[52] U.S. Cl. .................................. 324/71.1; 324/71.4; 266/99; 164/4.1
[58] Field of Search ................ 324/71.4, 71.1; 266/78, 266/80, 99; 164/4.1, 150

[56] References Cited

U.S. PATENT DOCUMENTS

| | | |
|---|---|---|
| 3,259,841 | 7/1966 | Proctor et al. |
| 3,395,343 | 7/1968 | Morgan et al. |
| 3,963,984 | 6/1976 | Coulter |
| 4,413,810 | 11/1983 | Tenberg et al. |
| 4,555,662 | 11/1985 | Doutre et al. |
| 4,600,880 | 7/1986 | Doutre et al. |
| 4,763,065 | 8/1988 | Hachey |

FOREIGN PATENT DOCUMENTS

| | | |
|---|---|---|
| 56-8527 | 1/1981 | Japan |
| 56-104504 | 8/1981 | Japan |
| 56-104505 | 8/1981 | Japan |
| 56-107541 | 8/1981 | Japan |

OTHER PUBLICATIONS

Ono, A., "Development of Direct Analysis Method for Molten Steel," pp. 51–57 (1989).
van der Plaats, G. et al., "Size Determination of Conductive Particles with a Coulter Counter," *Particle Size Analysis 1981*, pp. 208–215.

*Primary Examiner*—Jack B. Harvey
*Attorney, Agent, or Firm*—Panitch Schwarze Jacobs & Nadel

[57] ABSTRACT

A molten metal inclusion sensor comprises a single use disposable probe which is detachably connected to a support member. The probe may comprise a tube of heat resistant material having an inner electrode mounted on its interior wall and an outer electrode mounted on its exterior wall, the molten metal entering the tube interior through an orifice in its wall past a jet-preventer insert upon its immersion in the molten metal, whereupon the flow of metal with entrained inclusions is monitored by measuring the voltage between the electrodes. Alternatively the tube may be of electrically-conductive heat-resistant material and constitute the inner electrode. The flow may be assisted by a reduced pressure established within the tube, or may be slowed by a positive pressure to maintain the Reynolds number of the flow below 2000. The tube interior is divided by a narrow bore into two compartments so that metal enters one compartment and freezes in the bore so that it cannot enter the second compartment, protecting the vacuum source if provided and establishing the quantity of metal entering the probe. The orifice is closed by a meltable cover and the cover is protected by a meltable shield to enable the probe to be passed through an overlying slag layer without entry of slag to the probe interior. Various suitable materials are disclosed for the electrodes and for the body of the probe which should have a useful life in the bath of about 2 minutes.

17 Claims, 4 Drawing Sheets

SINGLE-USE DISPOSABLE MOLTEN METAL INCLUSION SENSOR

TECHNICAL FIELD

This invention relates to an apparatus for detecting the content of inclusions in molten metal, such as precipitated secondary phase particles, drops of slag, and/or air bubbles, during refining thereof, all of which cause a discontinuity in the flow of current in the sensing zoner and can therefore be sensed by measurement of this discontinuity. Hereinbelow, for convenience, all of these will be collectively referred to as "inclusions".

In general all such inclusions have a more or less deleterious effect upon the required technical properties of the metal, and it has become more and more essential to have accurate information as to their number and sizes, in order to confirm that the metal is sufficiently "clean" for its intended purpose, and also to show whether the processes employed are producing sufficiently "clean" metal.

INDUSTRIAL APPLICABILITY

The range of molten metals to which the present invention can be applied is broad and includes molten metals subjected to refining in steel manufacture, aluminium refining, copper refining, titanium refining, magnesium refining, alloys of these metals, and the like. However, in the following description, molten steel in steel manufacture will be used primarily as an example.

BACKGROUND ART

One prior art invention which relates to the present invention is described in U.S. Pat. No. 4,555,662, issued Nov., 1985, this patent disclosing a quantitative measurement method for inclusions, the method now being generally referred to as Liquid Metal Cleanliness Analysis (LiMCA for short). The LiMCA method and apparatus were originally developed for detecting nonmetallic inclusions during aluminium refining, but its application to iron and steel refining has also been investigated.

The LiMCA method is sometimes also referred to as the Electric Sensing Zone method (ESZ for short), the principle of the method being that when such an inclusion entrained in an electrically conductive fluid passes through an electrically-insulated orifice the electrical resistance of the fluid which is flowing through the orifice changes in proportion to the volume of the particle. The instantaneous change in the resistance is detected as a pulse in electrical potential between two electrodes on opposite sides of the orifice, and the number and size of the particles can be directly measured in the following manner.

First, if the particles are assumed to be spherical and of diameter d and the orifice is assumed to be cylindrical of diameter D, then the change R in the electrical resistance when a particle passes through the orifice is given by the following equation:

$$\Delta R = (4\rho d^3)/(\pi D^4) \quad (1)$$

Where $\rho$ is the electrical resistivity of the fluid.

In actual practice, Equation (1) must be corrected by a correction factor F(d/D), which is given by the following equation:

$$F(d/D) = [1 - 0.8(d/D)^3]^{-1} \quad (2)$$

Thus, $\Delta R$ is actually expressed by the following equation:

$$\Delta R = ((4\rho d^3)/(\pi D^4)) \times [1 - 0.8(d/D)^3]^{-1} \quad (3)$$

If the electric current through the orifice is I, then the pulse $\Delta V$ is the electric potential when a particle of diameter d passes through the orifice is given by the following equation:

$$\Delta V = I(\Delta R) \quad (4)$$

A previously-disclosed inclusion sensor probe which applies the above-described principles and for use with molten metal comprises a hollow inner first electrode made from an electrically-conducting, heat-resistant material, this inner electrode being supported inside a quartz tube and connected to an electrode rod through a graphite reinforcing member. An orifice is provided in a portion of the quartz tube near to its lower end, while a cylindrical layer which protects against slag is disposed around a central portion of the outside surface of the quartz tube. The tube is mounted on a water-cooled support apparatus through a coupler which is equipped with an O-ring to seal the joint between the tube and the coupler. The necessary outer second electrode consists of a rod separate from the probe and extending close to the orifice.

When a measurement is to be performed the inside of the hollow electrode, which serves as a chamber to receive the molten metal, is evacuated and the molten metal is sucked inside through the orifice. At this time, the change in electric resistance between the inner and outer electrodes is measured and amplified by conventional means, and the sizes and number of inclusions are determined.

The above-described sensor probe and others are used to perform continuous measurement by the LiMCA method in order to detect inclusions in molten aluminium and determine particle size distributions. Molten aluminium has a relatively low melting temperature of about 700° C., so there are a number of different materials available from which the probe and the electrodes can be made. However, the working temperatures of molten metal baths of metals like iron and titanium are much higher than for aluminium (above 1550° C.), and at such temperatures there are considerable problems with lack of resistance of the probe and the electrodes to heat, so that it is difficult to employ these known sensors.

The known probes for inclusion sensors as used hitherto for high melting point metals are all of the continuous measurement type, i.e. once the probe is immersed in the molten metal measurements are performed for a period of at least 30-40 minutes while being cooled with water, and usually this is the maximum useful life of such a probe. The known continuous measurement probes for inclusion sensors have the advantage that they can continuously monitor changes in the level of inclusions in molten metal, but have the following drawbacks.

(1) When used in a bath of high melting point molten metal, such as iron or steel, then in order to guarantee sufficient resistance to heat and reaction the body of probe must be made of a high-quality material, such as quartz, as a result of which the probe is expensive.

(2) When used with these high melting point metals, in spite of the fact that each probe is made of expensive materials, the probe still has life span of only 30-40 minutes, despite the use of water cooling.

(3) In order to provide sufficient heat resistance the probe support mechanism must be equipped with a water cooling mechanism. As a result, the probe and the probe support mechanism end up being large and difficult to handle, and a mechanism for raising and lowering the probe also must be large, so that equipment costs are high.

DISCLOSURE OF THE INVENTION

Accordingly, it is an object of the present invention to provide an inclusion sensor suitable for use with high melting point metals which has a less expensive probe and which is easier to handle.

In accordance with the present invention there is provided a molten metal inclusion sensor of the type which is immersed in a molten metal and detects inclusions in the molten metal by the electric sensing zone method, characterized in that a probe which is immersed in the molten metal for detection of the inclusions and a support mechanism for the probe are detachably connected with one another, and the probe is a single-use, disposable probe.

The probe may comprise a tube of electrically-insulating material which has the orifice for the inflow of molten metal formed in a portion thereof, and an electrically-conducting inner tube and/or an electrically-conducting outer tube, which respectively function as an inner and outer electrode, are mounted respectively on the inside and/or the outside wall of the electrically-insulating tube.

The probe may be made from an electrically-insulating tube which has the orifice for the inflow of molten metal sealed by an orifice cover of material of lower melting point than the metal, the electrically-insulating tube being sealed with reduced pressure inside it, and the structure being such that when the probe is immersed in the molten metal the orifice cover melts, and the molten metal flows into the tube interior assisted by the action of the reduced pressure.

The chamber inside the electrically-insulating tube may comprise two compartments which are connected by a bore of smaller cross-section area than the compartments, which bore constitutes a cooling zone, the orifice opening into one of the compartments whereby molten metal entering the first compartment freezes in the cooling zone to prevent its entry into the other compartment.

Thus, the present inventors performed investigations with the aim of solving the above-described problems, in the course of which they noted that the refining of metals such as iron and steel, which have a high melting point of at least 1500° C., is basically a batch treatment (e.g. processing in converter, RH treatment, etc.), and that during continuous casting the level of inclusions in a single batch does not greatly change. Namely, in the refining of steel for normal uses it is generally not necessary to constantly monitor the level of inclusions, even during continuous casting, and in many cases it is sufficient to determine a representative value for each batch. The present inventors then perceived of employing a single-use, disposable probe. The inventors found that it is effective to use a structure in which the probe is connected to a probe support mechanism by a quick-release joint, the probe comprising a molten metal inflow chamber having an orifice for detecting inclusions formed at its entrance; preferably a cooling region is provided in an exit portion of the chamber which connects it to a second chamber; also preferably the orifice is sealed in advance with an orifice cover, and the molten metal inflow chamber is first opened by melting of this cover when it contacts the molten metal. The structures in accordance with the invention therefore have among other advantages, the following:

(1) Decrease in Cost of Probe Body. The probe is a single-use, disposable member, so it can be made of less expensive material and can be decreased in weight. However, it still can be made with a life span of at least 2 minutes, and which may be as long as 10 minutes, and this is sufficient for it to be used in situations when a single measurement is sufficient.

(2) Increased Ease of Handling, Simplification of Handling Mechanism. As a single-use, disposable probe is light, it is easy to handle. Furthermore, as the probe also does not require a water cooling mechanism, the handling mechanism for the probe is simplified. It is also possible for an operator to perform measurements while holding the probe support mechanism in his hand.

In this manner a single representative measurement for a batch is made using the apparatus of the present invention, whereby decreases in the cost of the probe and in the handling mechanism are realized.

DESCRIPTION OF THE DRAWINGS

The prior art ESZ method and apparatus will now be described in more detail, and probes which are preferred embodiments of the invention will now be described, by way of example, with reference to the accompanying drawings, wherein.

DESCRIPTION OF PRIOR ART METHOD AND APPARATUS

Figure 1:
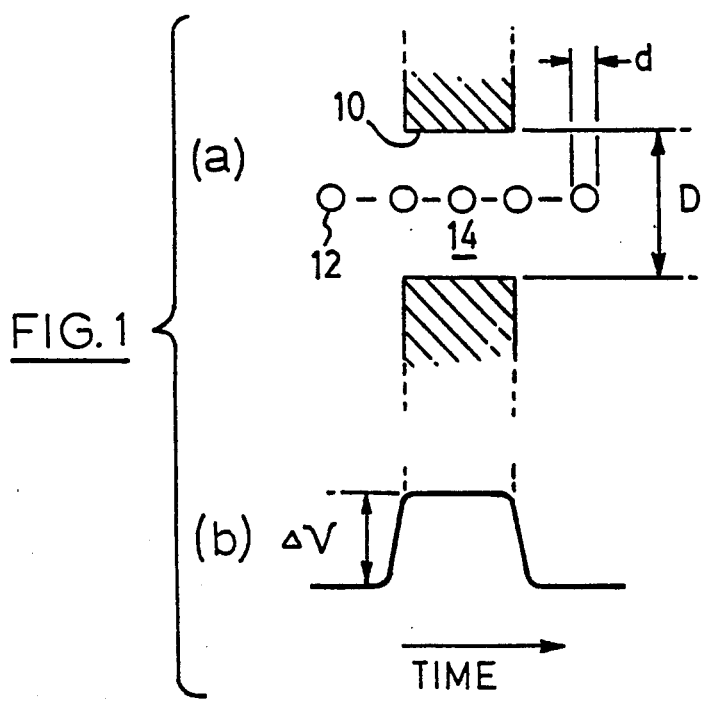
FIG. 1(a) and 1(b) are illustrations which explain the principles of inclusion detection by the ESZ method.

FIG. 1a illustrates an electrically-insulated orifice 10 of diameter D formed in a wall through which flows an electrically conductive fluid, namely molten metal. Non-conductive inclusion particles 12 of diameter d that are entrained in the fluid and flow through the orifice each give a respective resistance change and consequent electric potential pulse $\Delta V$ illustrated by FIG. 1b.

Figure 2:
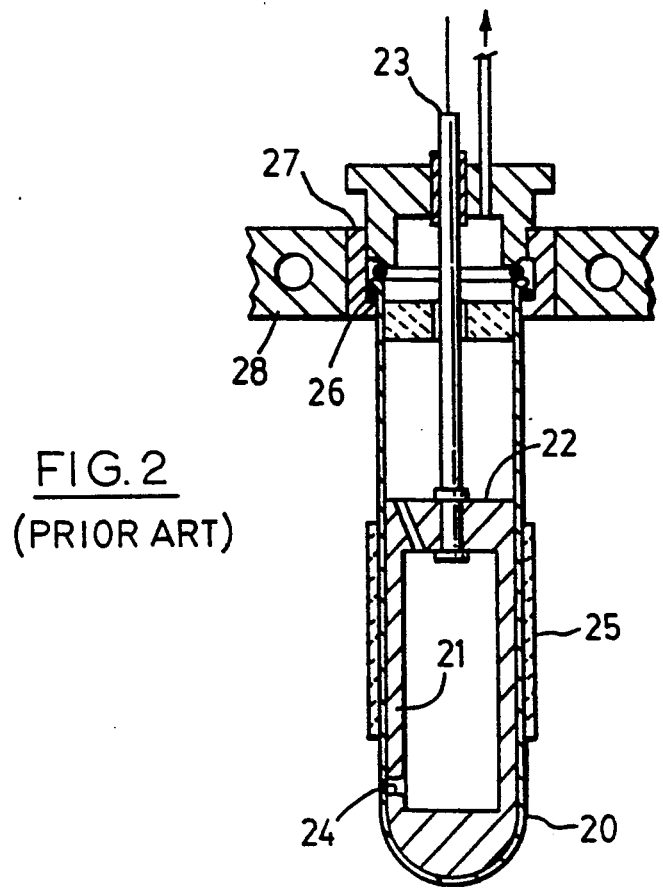
FIG. 2 is a longitudinal cross-sectional view of a continuous measurement prior art inclusion sensor probe which utilizes the ESZ method, and employs a separate outer electrode.

FIG. 2 is a schematic cross-sectional view of a prior art inclusion sensor intended for continuous measurement which applies the above-described principles. The outer electrode is separate from the other parts of the sensor and is not shown, but an inner hollow electrode 21 which is made from an electrically-conducting, heat-resistant material is supported inside a quartz tube 20 and is connected to an electrode rod 23 through a graphite reinforcing member 22. An orifice 24 is provided in a portion of the quartz tube 20 near to its lower end. A protecting layer 25 which protects against slag is disposed around the quartz tube 20. The quartz tube 20 is held by a water-cooled support apparatus 28 through a coupler 27 which is equipped with an O-ring 26.

BEST MODES OF CARRYING OUT THE INVENTION

Figure 3:
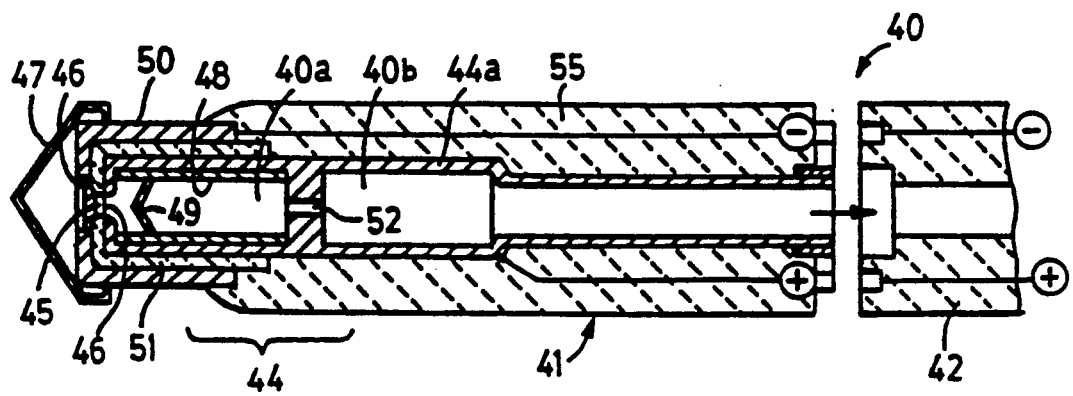
FIG. 3 is a similar view to FIG. 2 of a single-use, disposable probe in accordance with the present invention, which probe is connected to an external exhaust system.

FIG. 3 illustrates the structure of a sensor 40 of the invention which is employed with an external suction system. In the illustrated example, a probe portion 41 and a probe support portion 42 are detachably connected by fitting into one another, employing any suitable connection means which need not be specifically illustrated. As the present invention employs a single-use, disposable probe 41 the pressure seal between the probe and the support 42 need not be particularly tight but good electrical connection is essential to avoid the generation of spurious noise signals. The probe 41 includes a hollow cylindrical body member 44 providing a molten metal inflow chamber, which is divided into an outer chamber 40a and an inner chamber 40b by a cooling region 52 constituted by a bore of reduced cross-section area. The interior of the inflow chamber is connected to an external suction system (not shown) through the probe support mechanism 42 by any suitable means and a reduced pressure (vacuum) is maintained therein. An orifice cap 46 which is made of a material of lower melting point than the steel, aluminium for example, is disposed in an orifice 45 which is formed in the end of the body member 44. A conical-shaped slag breaker cover 47, also of lower melting-point material, is mounted on the end of the probe so as to also cover the orifice and the orifice cover 46. A hollow cylindrical electrode 48 of suitable electrically conductive material is mounted in the outer chamber 40a closely against the inner wall thereof and constitutes an inner electrode. A cylindrical external electrode 50 is mounted on the outside of the body member 44 and is separated therefrom by an interposed cylindrical electrically-insulating layer 51.

The slag breaker cover 47 and the orifice cap 46 both close the orifice 45 and maintain the vacuum produced by the suction inside the tube 44. Furthermore, they prevent slag from penetrating into the tube 44 when the probe is thrust through the layer of slag into the molten metal. Due to the action of these two members slag is prevented from entering the probe and adhering to the inner surfaces of the inner electrode 48 or the vacuum tube 44, which would give poor electrical conduction and unstable signals. It is desirable that the melting points of the slag breaker cover 47 and the orifice cap 46 be at least 10° C. lower than the melting point of the molten metal which is being measured. The thicknesses thereof are preferably in the range 0.1-1.0 mm. A thickness of this magnitude guarantees their strength prior to use and also guarantees that they will be melted quickly and permit the molten metal to flow into the probe interior during the available period of about 2 minutes.

In use the probe portion 41 is thrust at least one or two metres beneath the surface of the metal bath and, owing to the relatively high density of the slag layer and the steel, there is a substantial hydrostatic head present at the orifice 45; this hydrostatic head may with some embodiments be sufficient for the metal to flow into the probe. The passage of the metal is however facilitated by the presence of a reduced pressure inside the probe.

The tube 44 which constitutes the molten metal inflow chamber is a container for the purpose of introducing molten metal into the probe; the molten metal is drawn into the probe by the hydrostatic head and by the suction in the tube, and the particle diameter and number of inclusions in the molten metal are measured by the change in electrical resistance between the electrodes 48 and 50 as the inclusions flow through the orifice 45. For this purpose the electrodes are connected to exterior measuring apparatus by cables 56. The tube 44 is made from high melting point metal or an electrically-conducting ceramic and suitable materials are described in more detail below. The tube interior is directly connected to the exhaust system as shown by the arrow in the figure.

The transverse diameter of the body member 44 typically is about 2.5-10.0 cm, while its wall thickness is in the range 1-5 mm; the thickness of the electrode 48 typically is in the same range as the wall 44; the length of the chamber 40a typically is about 2.5-10 cm, while the cooling zone 52 which separates the outer chamber 40a and the inner chamber 40b has a cross-sectional area corresponding to a circle with a diameter in the range of 0.1-5 mm, and the length maybe in the range 1-10 mm. The inner chamber 40b typically has the same transverse dimensions as the outer chamber 40a and any required changes in its volume are produced by changes in its length. The dimensions and flow rate are made such that molten metal solidifies in the cooling zone 52 and is thus prevented from entering the chamber 40b and reaching the exhaust system. Furthermore, only an amount of molten metal equal to the volume of the outer chamber 40a is sucked in, and since the volume of this chamber is known, if the total number of pulses is counted, the number of inclusions per unit volume of the molten metal can be determined.

Figure 6:
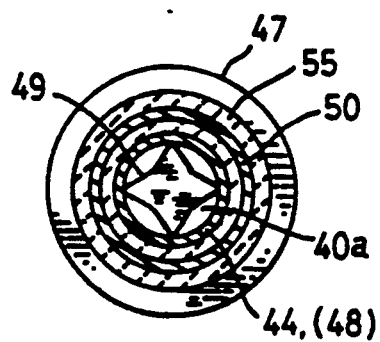
FIG. 6 is a cross-section taken on the line 6—6 in FIG. 5.

The layer 51 of insulating material typically has a thickness in the range of 5-15 mm, while the outer cylindrical electrode typically has a thickness in the range 2-6 mm. The specific thicknesses will depend to some extent on the material that is selected for these elements. The interior of the chamber 40a is provided with a conical star-shaped deflector member 49 disposed adjacent the orifice 46 with its conical end pointing toward the orifice, the member being shown in plan in FIG. 6. A suitable material for this is for example thin 1% carbon steel. The entering metal strikes this member and is deflected along the inside wall of the chamber, so that a jet cannot immediately reach the bore 52 and close it before the chamber is filled, which might reduce the amount of metal that can enter the chamber 40a within the available time.

A cylindrical layer or casing 55 of protective refractory material protects the probe (i.e. the tube 44, the cables 56, the exhaust connection, and the like) for the period for which the probe 41 is immersed in molten metal and is operative. It can be made of a refractory such as an MgO or $Al_2O_3$ type, or it can even be an inexpensive member made of layers of paper. A single-use, disposable probe of the invention is connected to the holder of a reusable probe support mechanism 42 by any suitable type of quick-release joint. After a measurement is performed the remains of the probe are removed from the holder and discarded, and when the next measurement is to be performed a new probe is mounted on the holder by the same operation.

Figure 4:
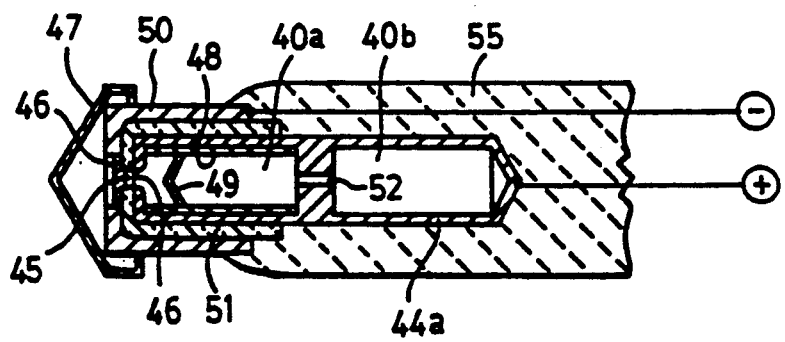
FIG. 4 is a similar view to FIG. 2 of a single-use, disposable probe in accordance with the present invention, which probe has an internal vacuum cell and therefore does not require an external exhaust system.

The apparatus illustrated in FIG. 4 has basically the same structure and mode of operation as that of the apparatus of FIG. 3, but the structure of the vacuum tube 44 is different. Thus, the inner chamber 40b of the molten metal inflow chamber 44 is previously evacuated and the probe is then sealed by the cap 45 after the inside thereof is reduced to a pressure of about 1–90 kpa. Accordingly, the outer chamber 40a which is sealed by the cap and the slag breaker 47 is also maintained under a vacuum, and in this state the probe is immersed in a molten metal. In the figure the method of connecting the probe to a probe support mechanism is not illustrated, but except for the absence of means to connect the probe interior to a suction system, the same holder as for the probe of FIG. 3 can be employed. The disposition of the outer electrode 50, the installation of the protective electrically-insulating layer 55, and the like can be the same as for the probe in FIG. 3.

As soon as the slag breaker and cap are melted molten metal is sucked into the outer chamber 40a of the tube 44; it solidifies in the cooling zone 52 and the sucking then stops with the required predetermined volume of metal in the probe. The ratio of the volumes of the outer chamber 40a and the inner chamber 40b determines the suction force and also determines the desired initial suction, but generally, it is desirable that the ratio of the volume of the outer chamber 40a to the volume of inner chamber 40b be at most 1:1. The dimensions of the cooling zone 52 and of the outer chamber 40a can be the same as for the probe of FIG. 3.

As described above, with the high hydrostatic head that is available when the probe is dipped deeply into the metal, it may not be necessary to provide a reduced pressure in the probe interior, the metal as it enters the first compartment 40a displacing the atmosphere in the compartment through the bore and compressing it into the second compartment 40b, which is therefore of sufficient volume for this to take place.

Figure 5:
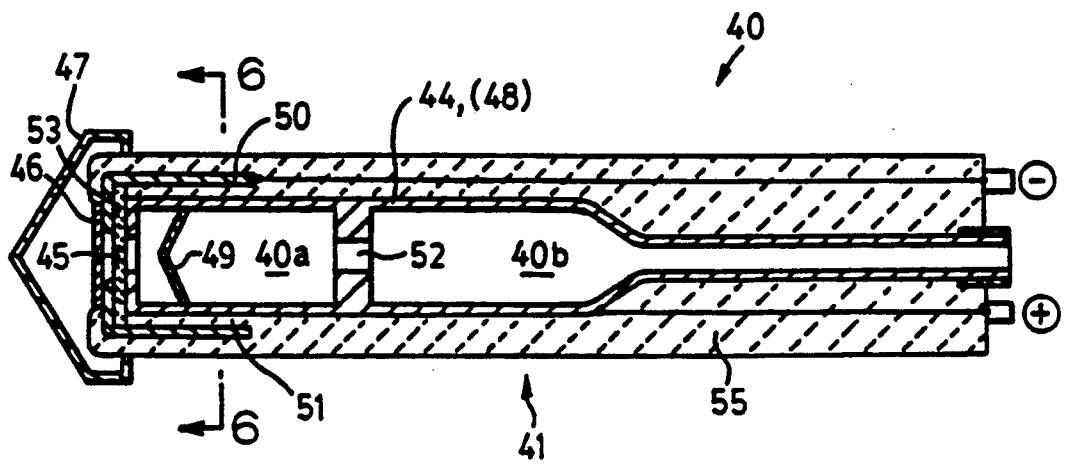
FIG. 5 is a similar view to FIG. 2 of another single-use, disposable probe in accordance with the present invention.

The embodiment of FIG. 5 also has basically the same structure and mode of operation as those of FIGS. 3 and 4 and similar parts are given the same reference whenever this is possible. It may be noted that all three of the embodiments are illustrated with their longest (longitudinal) dimension horizontal, but in practice they will be inserted vertically into the melt with the pointed slag breaker cover 47 entering first. The cylindrical body member 44 is made of steel so that a separate inner conductive electrode 48 is not required; the member is therefore given the reference 44(48). Good electrical contact is expected since portions of the molten steel entering the chamber 40a should "weld" to the steel interior wall. The inner and outer electrodes are separated and insulated electrically from one another circumferentially of the body 44(48) by the material of the refractory insulating layer 55, while the cylindrical insulating layer 51 of the two previous embodiments is reduced to a separate thin flat circular disc 53 having the orifice 45 at its centre. The outer electrode 50 can also be of steel and it will be noted that the layer 51 is extended as far as possible toward the nose of the device, so that as much as possible of the electrodes remains intact during the course of the usually available two minute immersion time.

The size of the orifice 45 that is required can vary relatively widely, depending upon the metal whose cleanliness is being investigated and the nature of the inclusions therein. A minimum value is therefore likely to be 200 microns, but some steels are found to have inclusions measuring as much as 250 microns, so that orifices as large as 1.2 mm may be required. Such large orifices may also dictate allowing the inflow to be produced by the hydrostatic head without the assistance of reduced pressure in the probe interior, or even with a positive pressure as is described below.

Some of the inclusions found in steel, such as alumina and aluminosilicates, are known to have a tendency to adhere to refractory materials and it is important to prevent this happening, since they may accumulate at the orifice and at least partly block it. One way of at least reducing this effect is to shape the orifice so that both the entrance and the exit are smoothly rounded, thereby avoiding turbulence and recirculation of the ingoing flow as much as possible; the choice of the material for the disc 53 will be affected by the ease of economically producing such a contoured aperture. For example, with a silica disc it is found possible to produce the orifice by first drilling a hole using a watchmakers diamond drill and then heating the edges of the hole with a micro-torch (oxy-acetylene) to partially fuse the silica and allow surface energy forces to shape it to the required contour. The initial size of the hole is chosen to achieve the desired final size of orifice. The use of a separate disc permits both entry and exit to be shaped conveniently in this manner before its installation in the probe.

Another consideration in avoiding turbulence and consequent potential for clogging is to keep the Reynolds number of the flow to less than about 2000, since beyond this value the flow tends to become turbulent even if the flow path is "streamlined" by the contouring of the orifice. The Reynolds number is given by the relation $$R = \frac{\rho U d}{\mu}$$

where
$\rho$ = density of fluid
U = mean flow velocity
d = diameter of orifice, and
$\mu$ = viscosity of the fluid It will be seen that $\rho$ and $\mu$ are set by the process being employed and only U and d can be determined by the design of the probe and are intimately related to one another. The choice of d is somewhat restricted in dependence upon the size of the inclusions to be measured, while the value of U can be controlled by the internal design of the probe, such as the ratio of the volumes of the two chambers 40a and 40b, the size of the bore 52 and the internal pressure in the chambers. If a large orifice is needed it may be necessary to provide a positive pressure in the probe interior to slow the flow to the required extent.

MATERIALS—ELECTRODES

In order to establish good electrical contact between the molten metal and the electrodes, without which the LiMCA signals will be obscured in a background of electrical noise, it is important that as much wetting as possible be established along the current path between the two electrodes and the electric sensing zone in between. From the point of view of choosing suitable electrodes, clearly they must not react with the melt to form an electrically insulating oxide, or other non-conducting layer. For example, an iron electrode in a copper melt containing dissolved oxygen will have its surface oxidized and then be unable to pass electrical current smoothly into the copper, and instead nickel should be used which forms a solid-solution range with copper and dissolves slightly. On the other hand, an electrode material that is inert to the melt and is also non-wetting (e.g. graphite in molten aluminium) is a poor candidate because any film of surface oxide, or even a thin gas boundary layer that inevitably forms when an object is pushed below the free surface of a metal, again resists the passage of electric current between the electrode and the melt.

Graphite also presents problems if the metal contains appreciable dissolved oxygen (e.g. above about 10 ppm) since there is a tendency to produce CO bubbles which can produce spurious signals, or even block the signal path completely. One helpful technique is to employ a brief heavy "conditioning" current prior to the application of the test current, as is employed in the LiMCA technique, which is believed to help "burn-out" local areas of oxides or gas films that otherwise produce increased electrical resistance between the electrode and the melt. It is useful also to choose an electrode material that is slightly reactive in a chemical sense to the molten metal. For aluminium mild steel electrodes can be employed, which form intermetallics such as $FeAl_3$, but simultaneously establish a good electrical and thermal path at the electrode/melt interface. In the case of molten steel, particularly aluminium killed steel with consequent low oxygen levels, graphite is a good choice in that it is a reasonably good conductor of electricity and dissolves in steel. Further, in low carbon melts, graphite has a contact angle with steel that is a little less than 90°, i.e., it is slightly wetting which is again helpful. The net effect of choosing graphite is an electrode which practically instantaneously establishes good contact. Further, as graphite does not melt at typical steel-making temperatures (1500°–1650° C.), it is very useful in that it can also be used to provide a mechanical support to the probe body when this is of an electrically insulating material such silica, the tube 44 being contained within the concentric inner and outer graphite electrodes in the embodiments of FIGS. 3 and 4. Silica melts at about 1740° C. and is certainly somewhat softened at steel bath operating temperatures, and therefore needs such support.

As described in connection with the embodiment of FIG. 5, an alternative to graphite can be steel or other high melting point metals such as tungsten or molybdenum. Such electrodes again have the advantage that they are "wet" by liquid steel and the molybdenum and tungsten have a finite solubility toward the molten steel which creates a perfect electrical contact once dissolution and removal of any oxide contaminants has taken place. In the case of steel an outer electrode of approximately pure iron will melt at 1540° C. rather than dissolve, which is resisted by the protective insulation layer 55, this dictating the choice of insulating refractories of appropriate thickness and properties for this purpose. Another suitable choice for electrode material is zirconium diboride ($ZrB_2$) but this is again an expensive material.

MATERIALS—ORIFICE SUPPORTS

A preferred electrical and thermal insulating material for the portion of the probe containing the orifice 45 is fused silica, whether as a tube or disc, despite its softening, because of its ready availability, lower cost and the relative ease of forming a contoured orifice. Moreover, silica is chemically attacked by iron and steel and it appears that the orifice is cleaned (reamed) by the flow of metal through it, so that good signals are obtained. The use of a high initial conditioning current is also useful, and it is found that maximising the time of contact between the silica and the steel also appears to improve performance, again indicating against too rapid a flow rate.

Other suitable materials are boron nitride (BN) which has been employed, and alumina ($Al_2O_3$). Orifices are readily made in boron nitride but contouring of the edges is more difficult; melts with high oxygen content (e.g. greater than 1,000 ppm) should also be avoided since otherwise the boron nitride is quickly corroded.

The invention will now be explained in greater detail by means of the following examples.

The concentration of inclusions in molten steel was measured using the probe of FIG. 4. The slag breaker 47 and the orifice cap 46 were made of aluminium, the vacuum tube 44 was made of stainless steel, the outer and inner electrodes were made of graphite, and the refractory insulator 51, in which the orifice was formed, was made of quartz. The orifice diameter was 300 micrometers, the outer chamber 40a had a volume of 50 $cm^3$, the inner chamber 40b had a volume of 100 $cm^3$, and the initial pressure within the tube was 75 kPa.

The probe was immersed in molten steel at 1565° C. in a tundish for continuous casting using a hand-held holder. The concentration and particle size distribution of nonmetallic inclusions in the molten steel were measured. Table 1 shows the composition of the molten steel.

TABLE 1

| Molten steel composition (Weight %) | | | | | |
|---|---|---|---|---|---|
| C | Si | Mn | P | S | sol. Al |
| 0.06 | 0.08 | 0.55 | 0.014 | 0.004 | 0.040 |

Figure 7:
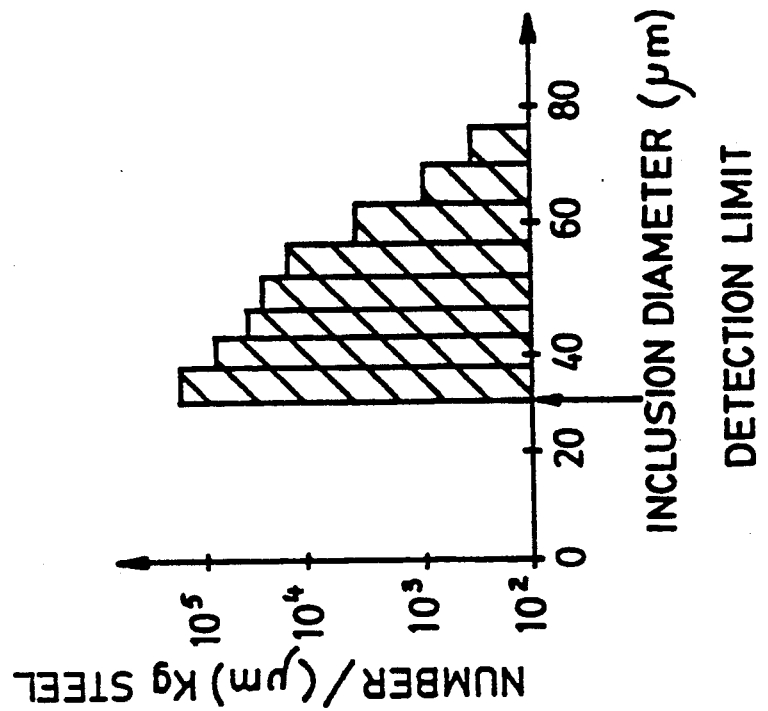
FIGS. 7 and 8 are graphs showing the particle size distribution of inclusions in the same molten steel as measured by an embodiment of the present invention and by a comparitive prior art probe.
Figure 8:
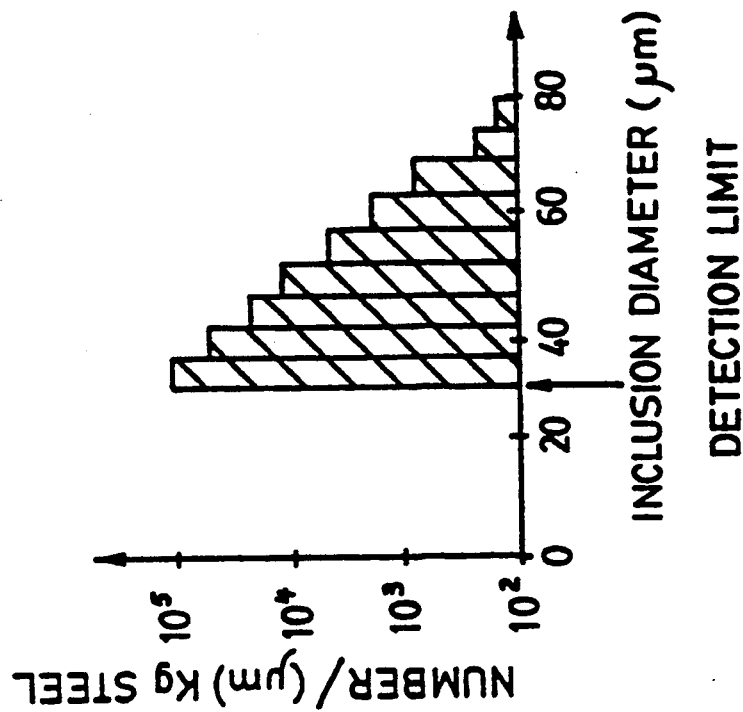

The particle size distribution of inclusions as measured when the probe was immersed in molten steel for 90 seconds and a steady state was reached is shown in FIG. 7. For comparison, the concentration and particle size distribution of nonmetallic inclusions in the same molten steel were measured by the ESZ or LiMCA method using the apparatus of FIG. 2. The results are shown in FIG. 8. It can be seen that nearly the same results were obtained as those shown in FIG. 7.

The probe of FIG. 2 had a probe support mechanism made of aluminium, a coupler 27 made of brass, a water-cooled holder 28 made of aluminium, an inner electrode rod 23 made of steel, an inner electrode 21 made of graphite, a quartz tube 20, a radiation shield made from ceramic fibers, a slag protection layer 25 made of high alumina cement, and an O-ring made of heat-resistant rubber.

Table 2 below shows a comparison of the weights, costs per probe, and total equipment costs for the probes in accordance with the present invention which are illustrated in FIGS. 3 and 4 and also for the comparative example of FIG. 2. The weight of the comparative example was 5 Kg, while the weight of the probes of the invention was 1 Kg; the cost per probe was reduced by approximately 10%, and the total equipment costs were reduced by 10-15%.

TABLE 2

| Probe Type | Length of Normal Operation from Start of Suction of Molten | Weight per Probe (kg) | Cost per Probe (Index) | Total Equipment Cost (Index) |
| --- | --- | --- | --- | --- |
| Present Invention (FIG. 4) | 2 | 1 | 10 | 90 |
| Present Invention (FIG. 5) | 2 | 1 | 11 | 85 |
| Comparative Example (FIG. 2) | At least 30 min. includes water cooling head | 5 (no reusable head) | 100 | 100 (needs raising and lowering device) |

Note:
Each index for the comparative example was given a value of 100.

It will be seen that, as described above, a probe in accordance with the present invention is relatively inexpensive as compared with the comparative example, but has a measuring accuracy which is fully adequate compared to that of a conventional probe for continuous measurement, and it is moreover easy to handle. Therefore, it has considerable advantages.

INDEX OF REFERENCE SIGNS

20: Prior art sensor—quartz tube
21: Prior art sensor—hollow inner electrode
22: Prior art sensor—graphite reinforcing member
23: Prior art sensor—electrode rod
24: Prior art sensor—sensing orifice
25: Prior art sensor—slag protective layer
26: Prior art sensor—O-ring
27: Prior art sensor—coupler
28: Prior art sensor—water-cooled support
40: Sensor of the invention
40a: Outer inflow chamber
40b: Inner inflow chamber
41: Probe portion of sensor
42: Probe support portion
44: Cylindrical body member
44 (48): The body member as inner electrode
45: Sensing orifice
46: Orifice cap
47: Slag breaker cover
48: Cylindrical inner electrode
49: Deflector member
50: Cylindrical external electrode
51: Cylindrical insulating layer
52: Cooling zone bore
53: Refractory disc with orifice
55: Protective refractory layer

We claim:

1. A molten metal inclusion sensor of the type which is completely immersed in a molten metal and detects inclusions in the molten metal by the electric sensing zone method, the sensor having a predetermined length and comprising a chamber (40a, 40b) having an orifice (45) in a wall thereof through which molten metal is drawn into the interior of the chamber, electrically conductive electrodes (48, 50) on opposite sides of the orifice, one of said electrically conductive electrodes extending adjacent to the orifice only partly the length of the sensor and means for measuring changes of potential between the electrodes produced by passage through the orifice of relatively non-conducting particles entrained in the molten metal, characterized in that a support (42) for a probe (41), which probe is immersed in the metal and which provides the chamber (40a, 40b), the orifice (45) and at least an inner electrode (48) are detachably connected with one another, and the probe is a single-use, disposable probe.

2. A molten metal inclusion sensor of the type which is immersed in a molten metal and detects inclusions in the molten metal by the electric sensing zone method, the sensor comprising a chamber (40a, 40b) having an orifice (45) in a wall thereof through which molten metal is drawn into the interior of the chamber, the chamber (40a, 40b) further including two compartments (40a, 40b) connected by a bore of (52) of smaller cross-sectional area than the compartments, which bore (52) constitutes a cooling zone, the orifice (45) opening into one of the compartments (40a) and the other compartment (40b) constituting a reduced pressure source, such that molten metal entering the first compartment (40a) freezes in the cooling zone to prevent its entry into the other compartment (40b), electrically conductive electrodes (48, 50) on opposite sides of the orifice, and means for measuring changes of potential between the electrodes produced by passage through the orifice of relatively nonconducting particles entrained in the molten metal, characterized in that a support (42) for a probe (41), which probe is immersed in the metal and which provides the chamber (40a, 40b), the orifice (45) and at least an inner electrode (48) are detachably connected with one another, and the probe is a single-use, disposable probe.

3. A molten metal inclusion sensor of the type which is immersed in a molten metal and detects inclusions in the molten metal by the electric sensing zone method, the sensor comprising a chamber (40a, 40b) having an orifice (45) in a wall thereof through which molten metal is drawn into the interior of the chamber, the chamber (40a, 40b) further including two compartments (40a, 40b) connected by a bore (52) of smaller cross-sectional area than the compartments, which bore (52) constitutes a cooling zone, the orifice (45) opening into one of the compartments (40a) and the other compartment (40b) constituting a reduced pressure source to the interior of which is connected an external source of reduced pressure, such that molten metal entering the first compartment (40a) freezes in the cooling zone to prevent its entry into the other compartment (40b) and its passage to the external source of reduced pressure, electrically conductive electrodes (48, 50) on opposite sides of the orifice, and means for measuring changes of potential between the electrodes produced by passage through the orifice of relatively nonconducting particles entrained in the molten metal, characterized in that a support (42) for a probe (41), which probe is immersed in the metal and which provides the chamber (40a, 40b), the orifice (45) and at least an inner electrode (48) are detachably connected with one another, and the probe is a single-use, disposable probe.

4. A molten metal inclusion sensor of the type which is immersed in a molten metal and detects inclusions in the molten metal by the electric sensing zone method, the sensor comprising a chamber (40a, 40b) having an orifice (45) in a wall thereof through which molten metal is drawn into the interior of the chamber, the chamber (40a, 40b) further including two compartments (40a, 40b) connected by a bore (52) of smaller cross-sectional area than the compartments, which bore (52) constitutes a cooling zone, the orifice (45) opening into one of the compartments (40a) such that molten metal entering the first compartment (40a) freezes in the cooling zone to prevent its entry into the other compartment (40b), electrically conductive electrodes (48, 50) on opposite sides of the orifice, and means for measuring changes of potential between the electrodes produced by passage through the orifice of relatively nonconducting particles entrained in the molten metal, characterized in that a support (42) for a probe (41), which probe is immersed in the metal and which provides the chamber (40a, 40b), the orifice (45) and at least an inner electrode (48) are detachably connected with one another, and the probe is a single-use, disposable probe.

5. A sensor as described in claim 4, wherein said probe (41) comprises a tube (44) of electrically-insulating material providing the chamber (40a, 40b), which tube has the orifice (45) for the inflow of molten metal in a portion thereof, characterised in that an electrically-conducting inner tube (48), which functions as an inner electrode, is mounted on the inside wall of the electrically-insulating tube.

6. A sensor as claimed in claim 5, wherein said probe (41) comprises a tube (44) of electrically-insulating material providing the chamber (40a, 40b) which tube has the orifice (45) for the inflow of molten metal in a portion thereof, characterised in that an electrically-conducting inner tube (48) and an electrically-conducting outer tube (50), each of which serves as a respective inner and outer electrode, are mounted respectively on the inside and the outside walls of the electrically-insulating tube.

7. A sensor as claimed in claim 4, characterised in that said probe comprises a tube (44) of electrically conducting material which provides the chamber (40a, 40b) and also functions as the inner electrode (48).

8. A sensor as claimed in claim 4, characterised in that the orifice (45) is sealed by an orifice cover (46) of material of lower melting point than the molten metal and the interior of the chamber (40a, 40b) is at a reduced pressure, the structure being such that when said probe is immersed in molten metal the orifice cover (46) melts and molten metal flows into the chamber (40a, 40b) through said orifice with the assistance of the reduced pressure.

9. A sensor as claimed in claim 4, characterised in that the orifice (45) is sealed by an orifice cover (46) of material of lower melting point than the molten metal and the interior of the chamber (40a, 40b) is at a reduced pressure provided by an external vacuum source, the structure being such that when said probe is immersed in molten metal the orifice cover (46) melts and molten metal flows into the chamber through said orifice with the assistance of the reduced pressure.

10. A sensor as claimed in claim 4, characterised in that the orifice (45) is sealed by an orifice cover (46) of material of lower melting point than the molten metal and the interior of the chamber (40a, 40b) is at a reduced pressure which has been produced in the chamber prior to the sealing of the orifice by the orifice cover (46), the structure being such that when said probe is immersed in molten metal the orifice cover (46) melts and molten metal flows into the chamber (40a, 40b) through said orifice with the assistance of the reduced pressure.

11. A sensor as claimed in claim 4, characterised in that the probe (41) is provided with an external shield member (47) covering the orifice (45) and of a material of lower melting point than the molten metal, the shield member (47) permitting the probe (41) to be passed through a layer of slag on the surface of the molten metal without entry of slag into the probe.

12. A sensor as claimed in claim 4, characterised in that the exterior of the probe (41) is covered with a layer of heat resistant material (55) to extend its useful life while immersed in the molten metal to a period of at least two minutes.

13. A sensor as claimed in claim 4, characterised in that the interior of the chamber (40a, 40b) is provided adjacent the orifice (45) with a deflector member (47) intercepting the metal entering the chamber and deflecting it to flow along the inner wall of the chamber.

14. A sensor as claimed in claim 4, characterised in that the orifice (45) has a contoured profile with both entrance and exit smoothly rounded to reduce turbulence of flow therethrough.

15. A sensor as claimed in claim 4, characterised in that the material of the chamber (40a, 40b) is selected from steel, molybdenum, tungsten, silica, boron nitride and Alumina.

16. A sensor as claimed in claim 5, characterised that the material of the electrode (50) or electrodes (48, 50) is selected from graphite, steel, molybdenum, tungsten and zirconium diboride.

17. A sensor as claimed in claim 4, characterised in that the rate of flow of the molten metal into the probe is such that the Reynolds number is less than 2,000.

* * * * *